United States Patent [19]

Wood

[11] Patent Number: 5,094,113

[45] Date of Patent: Mar. 10, 1992

[54] LEVER ACTION SAMPLER AND METHOD

[75] Inventor: Richard F. Wood, Miami, Fla.

[73] Assignee: General Oceanics, Inc., Miami, Fla.

[21] Appl. No.: 587,722

[22] Filed: Sep. 25, 1990

[51] Int. Cl.$^5$ .............................................. G01N 1/12
[52] U.S. Cl. .................................................. 73/864.67
[58] Field of Search ............ 73/864.63, 864.65–864.67;
220/326

[56] References Cited

U.S. PATENT DOCUMENTS

| | | | |
|---|---|---|---|
| 2,137,128 | 11/1938 | Blake | 73/864.65 |
| 3,489,012 | 1/1970 | Niskin | 73/863.31 |
| 4,037,477 | 7/1977 | Niskin | 73/864.67 |
| 4,091,676 | 5/1978 | Niskin | 73/864.67 |
| 4,106,751 | 8/1978 | Niskin | 251/174 |
| 4,302,974 | 12/1981 | Niskin | 73/864.62 |
| 4,593,570 | 6/1986 | Niskin | 73/864.67 |
| 4,744,256 | 5/1988 | Niskin | 73/864.66 |
| 4,852,413 | 8/1989 | Niskin et al. | 73/864.67 |
| 4,960,002 | 10/1990 | Isotalo | 73/864.67 |

Primary Examiner—Robert Raevis
Attorney, Agent, or Firm—Jack E. Dominik

[57] ABSTRACT

A lever action sampler having a body portion, usually tubular, and a pair of opposed end plugs for securing to the two ends of the body to thereby entrap a sample when activated is disclosed. The present invention utilizes a lever pivot assembly for an end plug at its upper portion, a lower end cap pivot assembly at the lower portion, both of which are pivotally secured to the end caps to permit the same to be locked/open for descending, and later closed for encapsulating the sample. The end caps are powered by means of a power spring and power spring cable operating exteriorly of the body, and actuated by means of a lever which cocks the unit into its unlatched and power spring preload functions, and thereafter secures a lanyard to either a rosette or to the sampler itself, and is subsequently fired by means of hitting the end cap of a push rod which release the lanyard or by releasing the lanyard from a rosette. The method contemplates the steps generally as itemized above.

3 Claims, 6 Drawing Sheets

LEVER ACTION SAMPLER AND METHOD

FIELD OF THE INVENTION

The present invention relates to samplers, and generally of the type which are used to capture samples of fluid at varying depths with varying amounts of salinity, temperature, and other properties at a preselected depth or a depth determined by instrumentation feedback to the surface. The subject devices are exemplified in U.S. Pat. No. 3,489,012 and U.S. Pat. No. 3,815,422, assigned to the assignee of the present patent application. Other prior art will be set forth below.

SUMMARY OF THE PRIOR ART

As indicated above, U.S. Pat. Nos. 3,489,012 and 3,815,422 are exemplary of the prior art. Also exemplary of the prior art is FIG. 1 in the attached drawings which will be described hereinafter. Other examples of the prior art appear in the following U.S. Pat. Nos.: 3,242,740; 3,425,664; 3,489,012; 3,815,422; 3,986,635; 4,037,477; 4,091,676; 4,106,751; 4,302,974; 4,347,751; 4,593,570; 4,744,256 and 4,852,413. The most exemplary of the prior art is U.S. Pat. No. 3,489,012 known as a Niskin bottle. It is powered by a "resilient rope" or rubber band which connects two end caps which engage the sampler body. With the upgrading and sophistication of analytical instrumentation in the last quarter century, the entrapping of "a resilient rope" such as a rubber band interiorly of the sample for even an hour during the time period between capturing the sample and analyzing the same can cause contamination and cross contamination giving spurious readings as to the mineral, chemical, and other content of the water sample. Accordingly, it is highly desirable to develop a sampler bottle which will have the advantages and features of the prior art, but which is externally powered and minimizes any contaminating or degradable material on the interior portion of the body as encapsulated by the end plugs.

SUMMARY OF THE INVENTION

The present invention is directed to a lever action sampler having a body portion, usually tubular, and a pair of opposed end plugs for securing to the two ends of the body to thereby entrap a sample when activated. The present invention utilizes a lever pivot assembly for an end plug at its upper portion, a lower end cap pivot assembly at the lower portion, both of which are pivotally secured to the end caps to permit the same to be locked/open for descending, and later closed for encapsulating the sample. The end caps are powered by means of a power spring and power spring cable operating exteriorly of the body, and actuated by means of a lever which cocks the unit into its unlatched and power spring preload functions, and thereafter secures a lanyard to either a rosette or to the sampler itself, and is subsequently fired by means of hitting the end cap of a push rod which release the lanyard or by releasing the lanyard from a rosette. The method contemplates the steps generally as itemized above.

In view of the foregoing it is a primary object of the present invention to manufacture a product and develop a method of encapsulating a sample of water in which the fluid itself is entrapped in a generally inert environment of an essentially tubular body with closure end plugs.

A related object of the present invention is to provide such a lever activated sampler which is economical to produce and competitive with pre-existing samplers, and yet offering the distinct advantage of an inert environment in which the sample is encapsulated.

Yet another object of the present invention is to provide a sampler with the above advantages which can be either mounted to a rosette, or which can be, in single fashion, sent down a support wire to the preselected depth at which time the sampler is activated and closed.

BRIEF DESCRIPTION OF THE DRAWINGS

Further objects and advantages of the present invention will become apparent as the following description of an illustrative embodiment proceeds, taken in conjunction with the accompanying drawings, in which.

DESCRIPTION OF A PREFERRED EMBODIMENT

Figure 1:
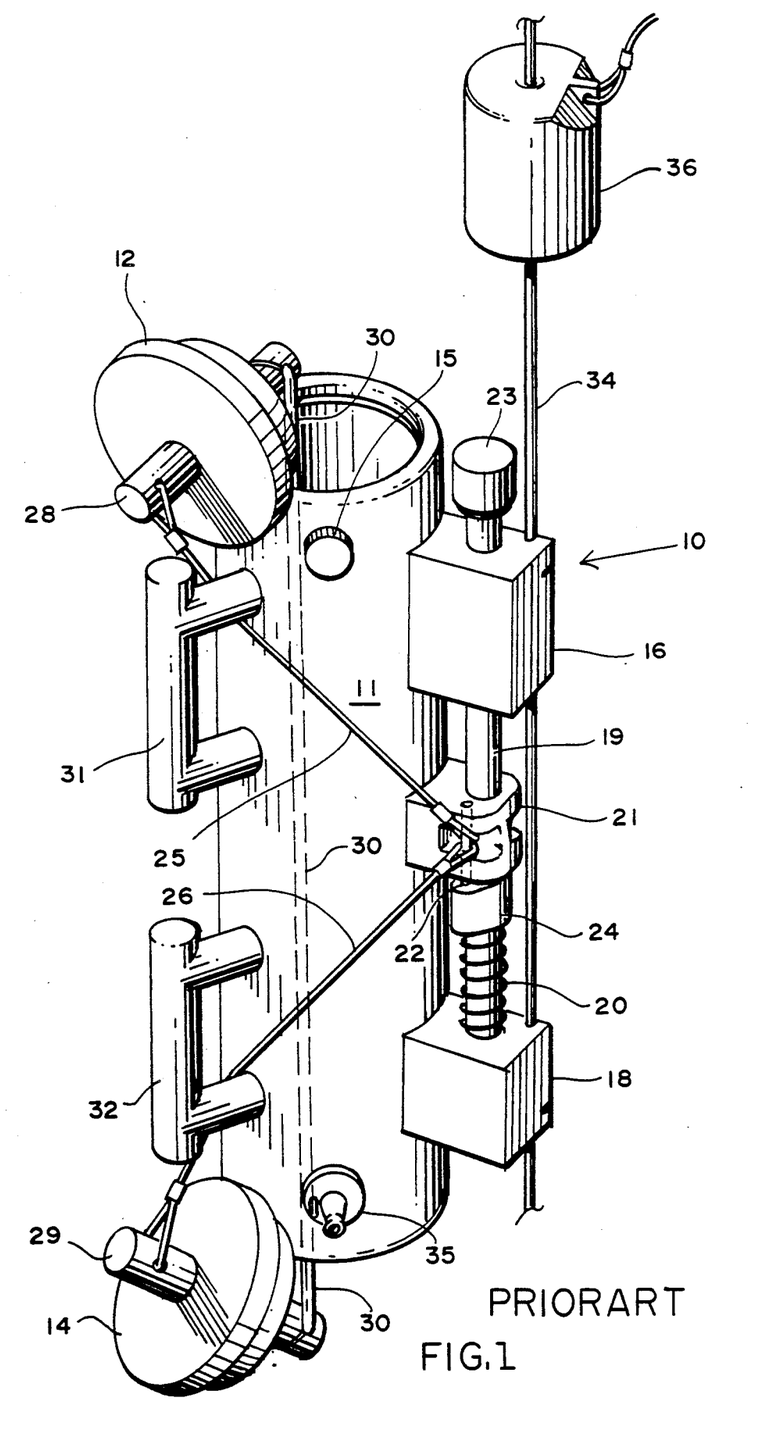
FIG. 1 is a partially diagrammatic perspective semi-exploded view of an example of the prior art.

The preferred embodiment will be best understood after a description of the prior art, as set forth generally in FIG. 1. There it will be seen that the prior art sampler 10 has a body 11 with an upper end plug 12 and a lower end plug 14. Provision is made on the body 11 for an upper air vent screw 15, and a lower sample drain 35. Means are provided in the form of an upper mounting block 16 and a lower mounting block 18 to secure the push rod 19 as dictated by the push rod spring 20. A center release block 21 is provided to secure the lanyard 26. The center release block 21 includes a release pin 22, and the push rod 19 has at its top a push rod cap 23. The thumb block 24 is employed to engage the lanyard when the release pin 22 is moved into the open position.

As seen in the prior art sampler 10, there are two lanyards, the upper release lanyard 25 and the lower release lanyard 26. Each of these prior art release lanyards 25, 26 are geared to respectively the upper cap handle 28 and the lower cap handle 29. Provision is made, as set forth in the description of the prior art above, for a closure band 30 which is usually in the form of a surgical rubber retractable band, and extends through the interior portion of the body 11 of the prior art sampler 10. Provision is also made for an upper carrying handle 31, and a lower carrying handle 32.

Further it will be seen that the prior art sampler 10 is mounted to a support wire 34 by means of clamping members (not shown) which are located interiorly of the upper mounting block 16 and the lower mounting block 18. A messenger 36 slides over the support wire 34 and, upon striking the push rod cap 23, depresses the push rod 19, thereby opening the release pin 22 to permit the lanyard end loops to be released whereupon the closure band 30 pulls the two end plugs 12, 14 into a position where they close the ends of the sampler body 11. At this point in time, the sample may have been encapsulated at any depth in the sea water which might be as much as three miles or more. It takes some time to bring the prior art sampler 10 back to the surface and then to drain the same to develop a sample which can be analyzed with state of the art analytical instrumentation. During this time period even the finest surgical rubber retractable band or its equivalent will give off minute amounts of its surface, indeed even in molecular form, and they will go into the solution of the sample. Such ingredients in the sample, even though relatively inert, can give spurious false readings when the sample is analyzed. To this end the present invention is directed primarily to producing a sampler in which the interior portion can be made of an inert material, and the enclosure members being made of a highly inert material, to the end that cross contamination and leaching of the sampler body and the sampler end plugs is held to an irreducible minimum.

Figures 2, 3, 4, 5, 6, 7:
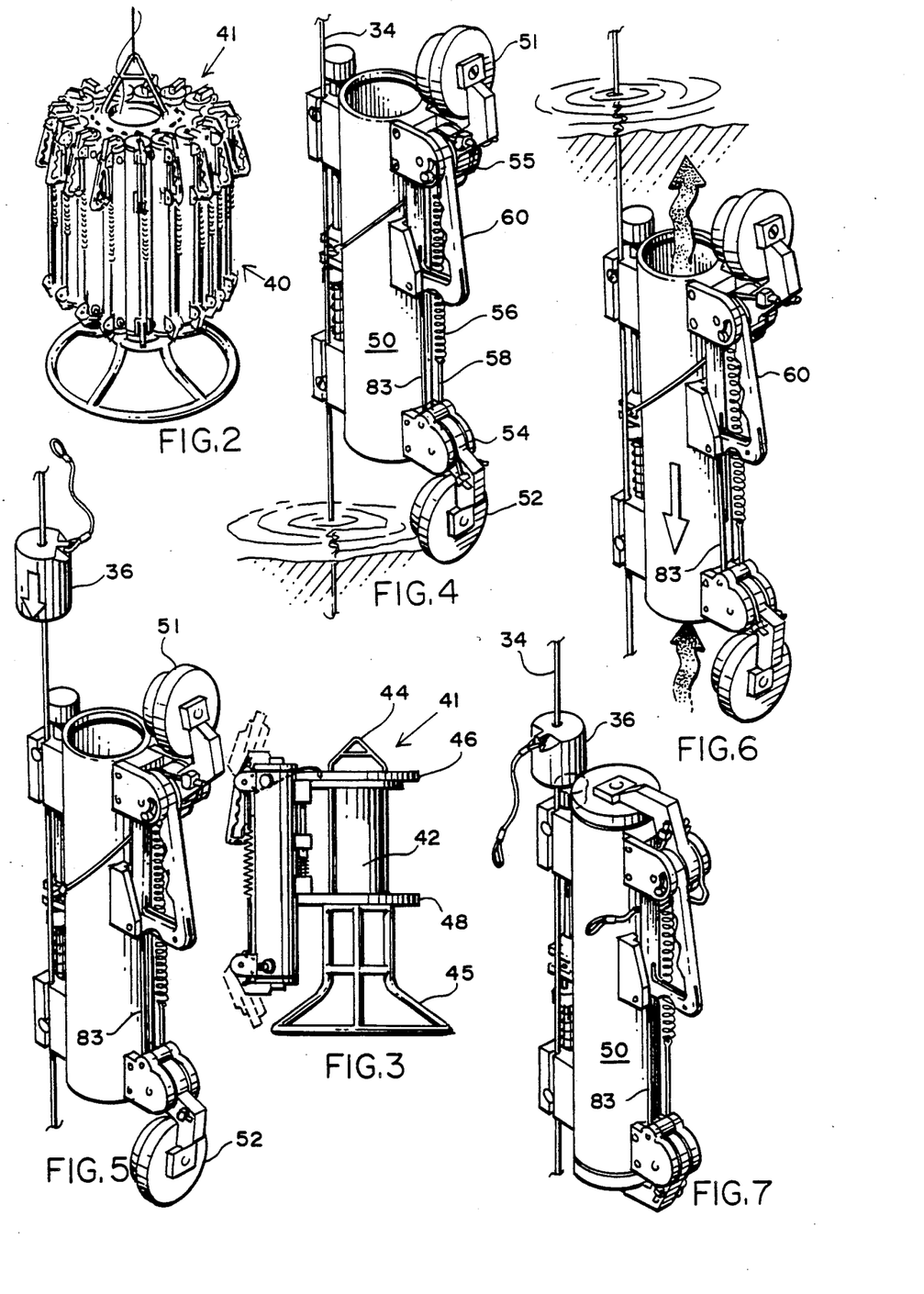
FIG. 2 is a perspective view of a typical sampler array containing a plurality of the lever action samplers 40.
FIG. 3 is an interior view of the sampler array shown in FIG. 1 but illustrating the central pylon, hanger, stand, mounts, and means for securing an exemplary lever action sampler.
FIG. 4 is a perspective view of the subject lever action sampler secured to a support wire ready for immersion into a fluid such as the ocean.
FIG. 5 is a view sequential to that of FIG. 4 illustrating how a messenger is sent down to activate the lever actuated sampler to encapsulate a sample.
FIG. 6 is a view of the sampler passing down through the water and the water passing through the central portion with the white arrow showing the direction of the sample water and the black arrow showing the direction of the lever actuated sampler.
FIG. 7 is a view subsequent to that of FIGS. 5 and 6 illustrating the unit being closed and the messenger riding on top of the push rod cap.

The lever action samplers 40 of the present invention are normally mounted on a sampler array 41 as illustrated in FIG. 2. More specifically, the illustration of FIG. 3 shows the sampler array 41 and its central pylon portion 42 to which, at the top, a hanger 44 is provided. The hanger 44, in turn, is secured to a cable on the mother ship which will typically drop the array into the ocean for sampling purposes. The lower portion or stand 45 permits the unit to stand on the mother ship, or be loaded even prior to being loaded on the ship with the inventive lever action samplers 40. Also on the sampler array 41 is an upper mount 46 and a lower mount 48. These mounts, as shown in FIG. 3, are used to secure the single lever action sampler 40 illustrated in FIG. 3.

Turning now to FIG. 4, it will be seen that the lever action sampler 40 has a body 50. The body 50 is shown as being cylindrical in cross-section and tubular in length. Modifications and other alternatives are contemplated, but the most economical and practical found thus far have been the tubular member having a circular cross-section.

An upper end plug 51 and lower end plug 52 are provided at the remote ends of the body 50. The lower end cap pivot assembly 54 secures the lower end cap 52 pivotally to the body 50. The lever pivot assembly 55 secures the upper end plug 51 in its pivot position, with both end plugs 51, 52 being coordinated by the power spring 56 along with the power spring cable 58 to simultaneously secure the respective end plugs 51, 52 to the end portions of the body 50 for encapsulating and entrapping a sample. As shown in FIG. 4, the lever action sampler 40 is positioned for lowering into the fluid shown diagrammatically in the lower portion of FIG. 4.

FIG. 6 shows the lever action sampler 40 being lowered beneath the surface of the fluid and in white arrows the fluid passing upwardly through the body 50, and the black area indicating the movement downwardly. FIG. 5 illustrates the messenger 36 as it is about to engage the end cap 71 of the push rod 70 against its lanyard release mechanism. Finally, FIG. 7 shows the lever action sampler 40 closed.

Figures 8, 9, 10:
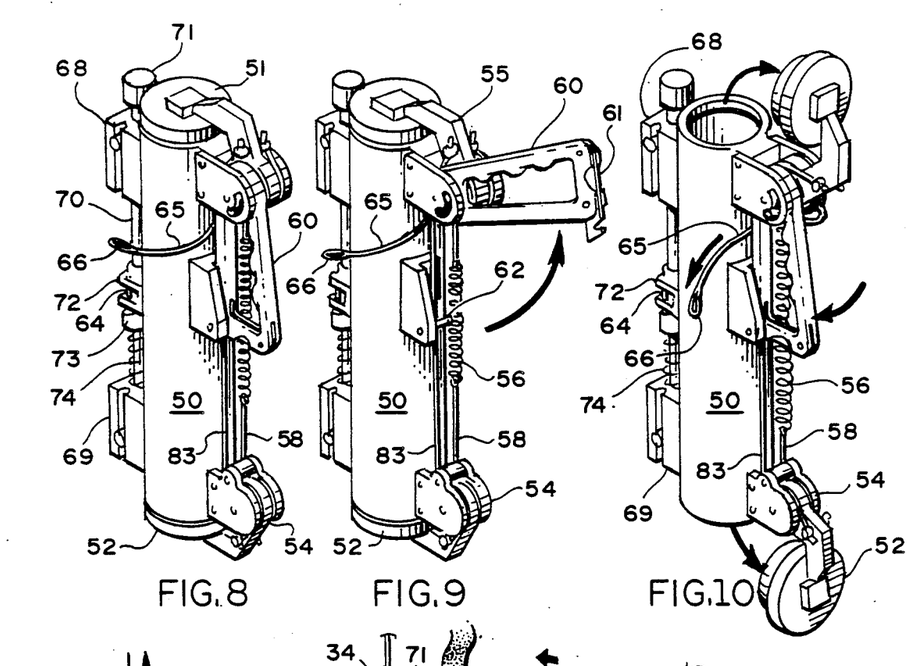
FIG. 8 is a view in connection with FIGS. 9, 10, 11, 12 and 13 showing the sequences of operation, FIG. 8 illustrating the transport configuration.
FIG. 9 illustrates the unlatching configuration of the lever operated sampler.
FIG. 10 illustrates the power spring preloading of the unit in operation.

Turning now to FIGS. 7–13, the sequence of operation will be described. Initially the lever action sampler 40, as shown in FIG. 8, is in the transport configuration. The lanyard 65 and its lanyard loop 66 are mounted loosely. When it is desired to activate the lever action sampler 40, the first step is the unlatching step as illustrated in FIG. 9. This is achieved by moving the loading lever 60 upwardly after the loading lever latch 61 has been disengaged from the loading lever latch pin 62. Again the lanyard 65 and lanyard loop 66 are loose, but intended for subsequent securement.

Thereafter as illustrated in FIG. 10, the power spring preloading step is undertaken. At this point the loading lever 60 is depressed, and the latch 61 engages the latch pin 62 again thereby preloading the power spring 56. As shown by the arrows, the upper end plug 51 and lower end plug 52 are pivoted rearwardly to their full open position.

Figures 11, 12:
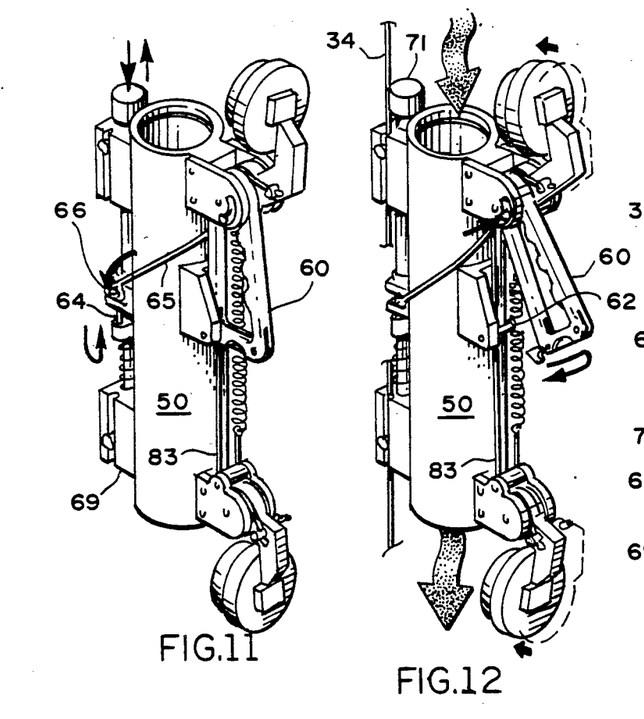
FIG. 11 illustrates the lanyard securing step in which the lanyard is optionally secured to a lanyard pin.
FIG. 12 is the lanyard loading phase just prior to dropping the sampler into the water and partially closing the two end plugs.
Figure 13:
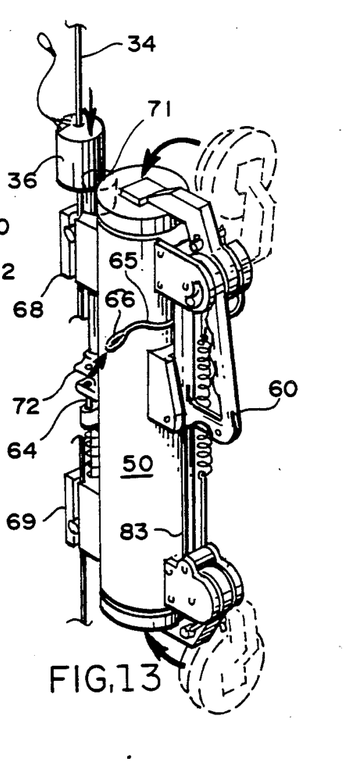
FIG. 13 finally shows a messenger engaging the end cap of the push rod and activating the end plugs from the configuration shown in the phantom lines to securing on the body portion and entrapping the sample.

Thereafter the lanyard securing step is taken as illustrated in FIG. 11. At this point the operator engages the thumb portion 73 of the push rod 70 and releases the center release block 72 to a point where the lanyard loop 66 can be engaged on the release pin 64. Thereafter, when the loading lever 60 is again removed and repositioned as shown in FIG. 12, the lever action sampler 40 is ready for immersion into the fluid such as the sea. Once the lever action sampler 40 is at the position in the fluid where the sample is to be taken, a messenger 36, as illustrated in FIG. 13 is dropped and engages the push rod cap to release the lanyard as shown. Subsequently, not as shown in FIGS. 8–13, the sample is removed in the same fashion as shown in the description of the prior art in FIG. 1 with the vent 15 being opened, and the sample drain 35 being open to release the sample for containment and further processing and analyzing.

Figure 14:
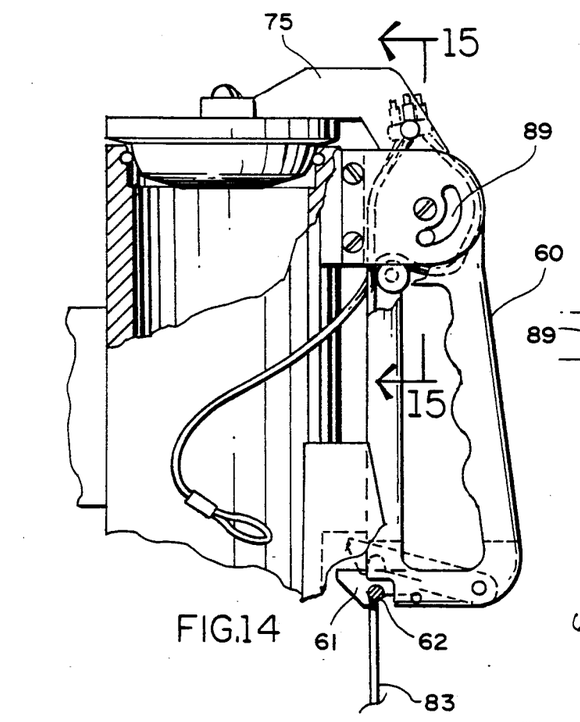
FIG. 14 is a front elevation, partially broken, showing the loading lever and the lever pivot assembly along with the latch shown in phantom lines.
Figure 15:
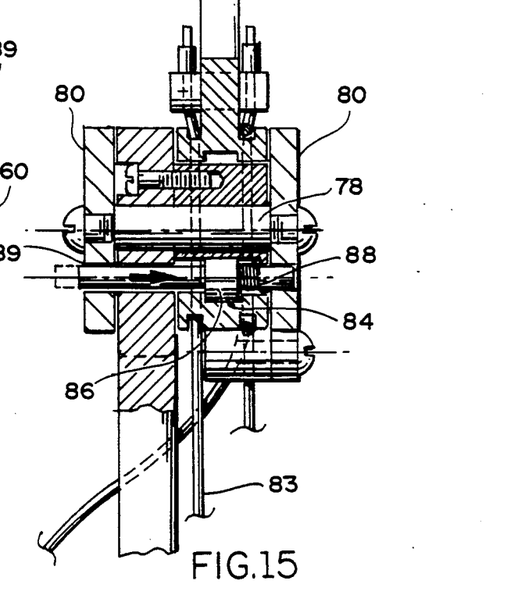
FIG. 15 is a transverse enlarged sectional view of the upper portion of the lever pivot assembly taken along section line 15—15 of FIG. 14.
Figure 18:
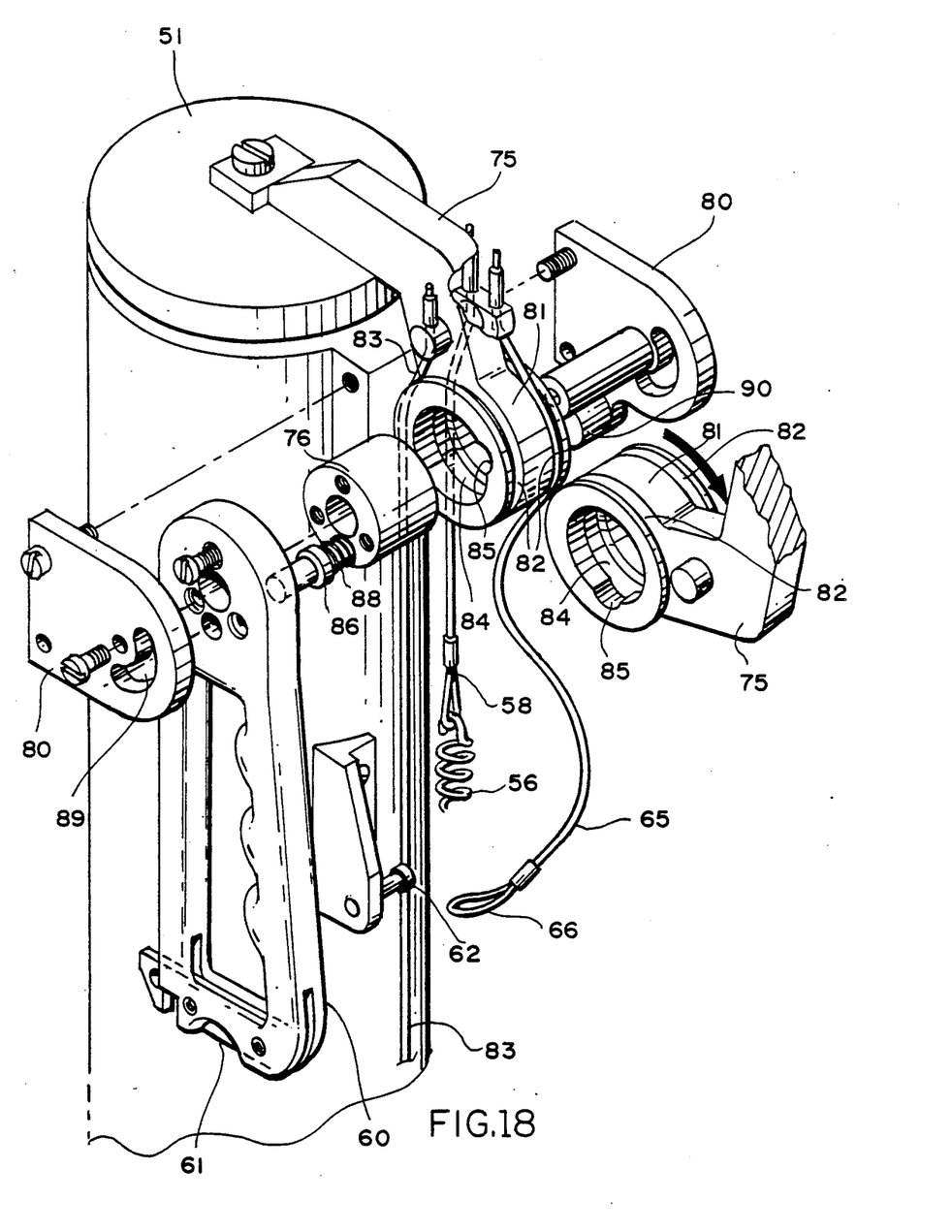
FIG. 18 is an isometric exploded View of the lever pivot assembly showing its internal parts, the power spring, the lanyard, and the latch mechanism for the lever.

The basics of the lever pivot assembly 55 are shown in FIGS. 14–17, but most importantly in the exploded view in FIG. 18. Referring firstly to FIG. 14, it will be seen that the loading lever 60 is at the lower portion of the lever pivot assembly 55. The loading lever 60 is secured to the pressure arm 75 which, in turn, drives and orients and closes the upper end plug 51.

Figures 16, 17:
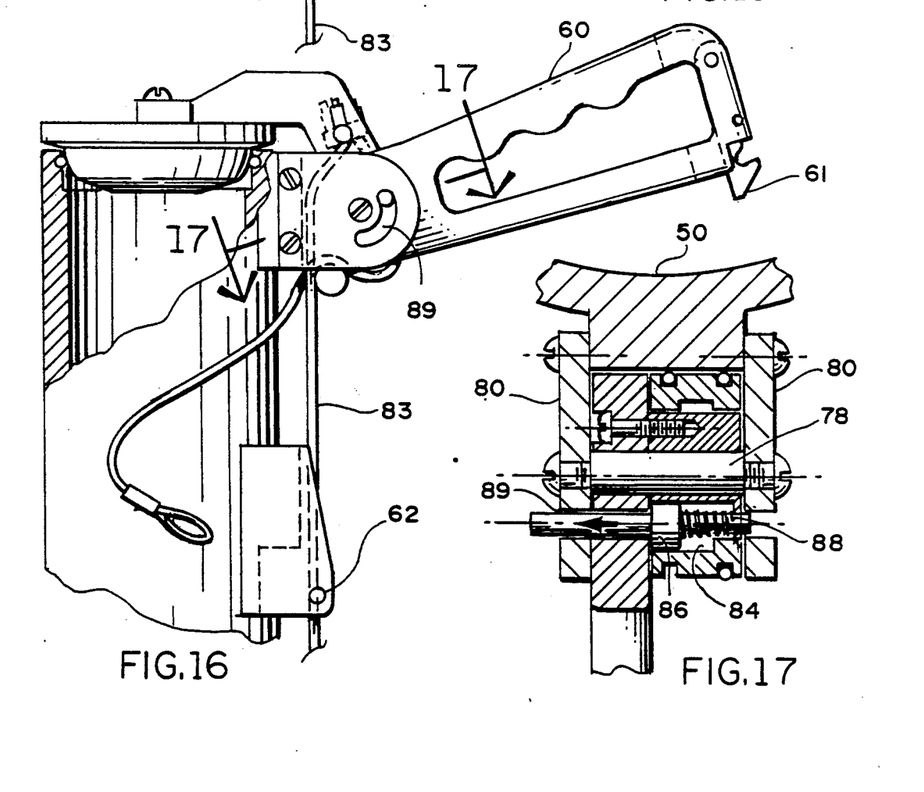
FIG. 16 is a view similar to that of FIG. 14, but showing the loading lever in the configuration essentially as that shown in FIG. 9.
FIG. 17 is yet another sectional enlarged view taken along section lines 17—17 of FIG. 16.

The parts of the lever pivot assembly 55 are shown generally in cross-section in FIGS. 16 and 17 and in exploded relationship in FIG. 18. When the lever action sampler 40 is being opened, as shown in FIG. 16, the loading lever 60 is rotated downwardly in order to activate the upper pressure arm 75 to open the upper end plug 51.

Turning now to FIG. 18, it will be seen that the loading lever 60 and its associated latch 61 are secured by means of latch pin 62. The cam lock pin assembly 86 has a cam lock in the form of an enlarged collar, and is held in position by means of a cam lock spring 88. The cam lock pin assembly 86 slides in a crescent-shaped opening pin guide 89 provided in the mounting bracket 80 shown at the left-hand portion of FIG. 18. The drive pin bushing 76 which is secured to the upper end plug 51 by means of the upper pressure arm 75, is also secured to the power spring cable pulley 81 portion of the pressure arm 75, and includes cable grooves 82 to assist in guiding and actuating the cable which in turn is secured to the power spring 56.

An interior groove 84 in the power spring pulley 81 is provided interiorly of the power spring cable pulley 81 to receive the cam lock pin 86 collar portion assembly when the lever 60 is to rotate freely. When the lever 60, however, is to engage and rotate the power spring cable pulley 81, the cam lock 86 is positioned in the engaging groove 85 of the interior portion of the power spring cable pulley 81. A crescent shaped pin guide 89 (FIG. 16) contains the cam lock spring assembly 86 and a power spring cable guide 90 (FIG. 18) is provided for the power cable to loop around.

Figure 19:
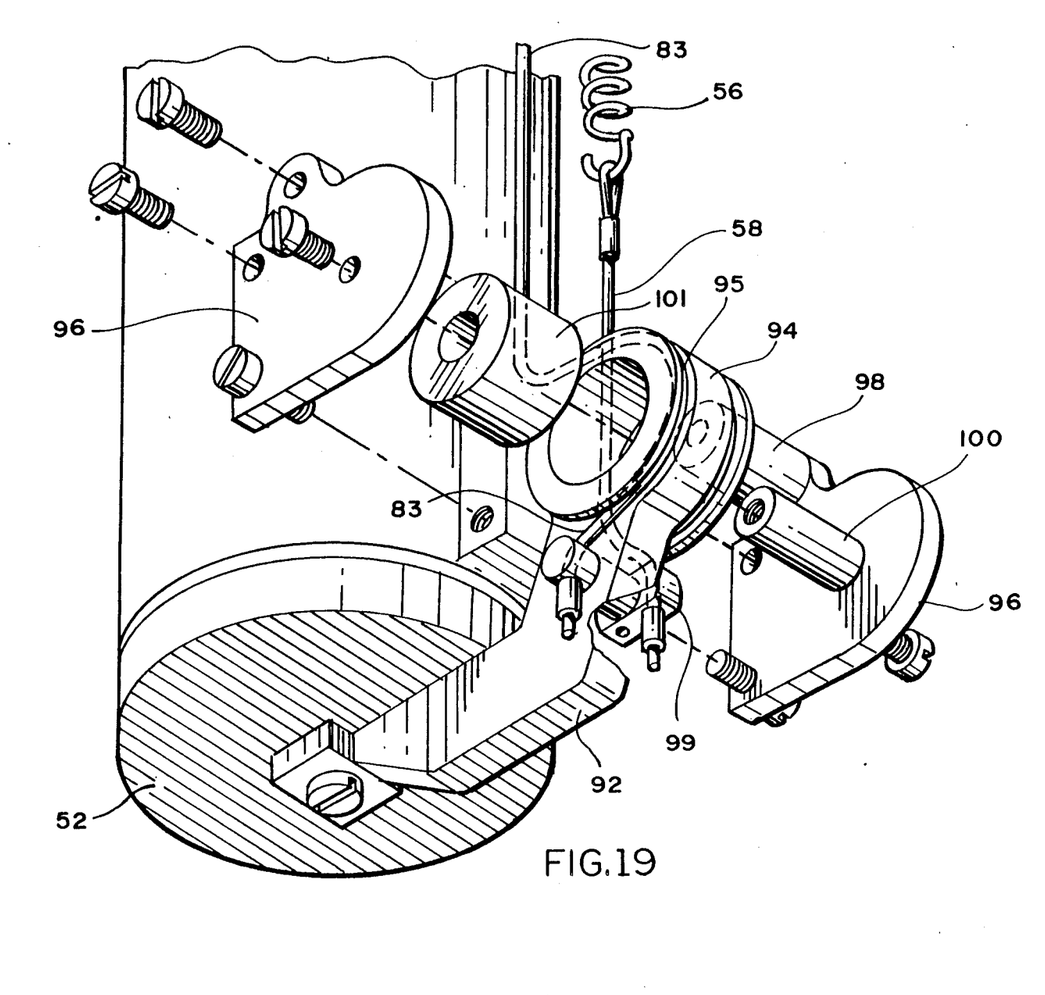
FIG. 19 illustrates the lower end plug and the lower end cap pivot assembly in isometric and exploded form.

As shown in FIG. 19, the lower pressure arm 92 secures the lower end plug 52 to the lower portion of the body 50. A lower power spring cable pulley 94 is provided with power cable grooves 95, and secured by brackets 96 to the body 50 in much the same fashion as the lever pivot assembly 55 described above. The lower cable guide 98 functions in much the same fashion as the upper cable guide 90, and an anchor assembly 99 for the power cable 58 secures the lower ends of the power cable 58 to the lower power spring cable pulley assembly 94 which is secured to the sampler body 50 by means of lower brackets 96. An axle 100 secures the elements of the lower end cap pivot assembly 54 in their operative relationship, with a lower bushing 101 mounted interiorly of the lower power spring cable pulley 94 and coaxially on the lower axle 100.

The method of the present invention is directed to the steps essentially as shown in connection with the description of FIGS. 8–13. Primarily the method comprises taking a sampler and utilizing an externally mounted power spring 56, and securing the same by means of a lever pivot assembly 55 to the upper end plug 51, and securing the lower end cap pivot assembly 54 in its lower position and mounted on the sampler body 50 and secured to the power spring 56. Thereafter, the sampler 40 is unlatched from the transport configuration in anticipation of power spring preloading by means of firstly unlatching lever latch 61 and then raising rotating upwardly the lever 60, and then thereafter closing the same when, as shown in FIG. 18, the cam lock pin assembly 86 is shifted into and out of the locking or engaging groove 85, or interiorly into the free rotate groove 84 actuated by cam lock spring 88. Thereafter, the step as shown in FIG. 11, namely the lanyard securing step is performed where the lanyard is either secured to the center release block 72 as shown in FIGS. 11 and 12, or secured to the array 41 essentially as shown in FIGS. 2 and 3. Finally, the loading lever 60 is rotated downwardly and the lanyard loading step as illustrated in FIG. 12 is accomplished, by re-engaging the latch 61 with the pin 62 sampler 40 is then lowered into the fluid to a depth where it is desired to actuate. At this point, when the sampler 40 is to be closed, the messenger 36 is sent down the support wire 34, it engages the push rod cap 23, and the lanyard is released permitting the power spring 56 through the power spring cables 58 to close the upper end plug 51. The lower end plug 52 on the tubular body portion 50 of the lever action sampler 40 is actuated by the lower end plug control cable. Closing can also be actuated by removably securing the lanyard to the array 41.

It will be understood that various changes in the details, materials and arrangements of parts which have been herein described and illustrated in order to explain the nature of the invention, may be made by those skilled in the art within the principle and scope of the invention as expressed in the appended claims.

What is claimed is:

1. A lever action sampler comprising, in combination,
   a tubular body having an upper end plug end and a lower end plug end,
   an upper end plug and a lower end plug hingedly secured to the body and proportioned to sealingly engage the upper end plug end and lower end plug end,
   means operatively secured to each of said end plugs to receive a power cable,
   a power cable having a central power spring external to the body and essentially parallel and in spaced relationship to the body,
   a lever pivotally and selectively coupled to one of said end plugs for rotating the same and simultaneously loading the power spring,
   a lanyard coupled to said lever actuated end plug to secure the same in its opened relationship to the body,
   said power cable being secured to the other end plug of said body remote from the lever to secure the same in its open configuration simultaneously with that of the lever actuated end plug,
   a lanyard anchor,
   and means for removably securing said lanyard to said anchor which, when released, releases the lanyard and permits the power spring through the power cable to pivotally drive the end plugs to their closed position thereby plugging each end of the body and capturing a sample.

2. In the lever action sampler of claim 1,
   a lever pivot assembly,
   said power cable being anchored to the lower end plug,
   said power cable being reaved around the lever pivot assembly,
   lower end plug control cable being positioned in grooves on the lower pivot assembly and the lower end cap pivot assembly to apply a tensional force to the power spring when the lever is actuated to open the sampler by pivoting the upper end plug and lower end plug into the open position.

3. The method of operating a lever action sampler having a tubular body portion, a pair of end plugs pivotally secured to each end of said body portion, a power spring and cable assembly secured externally of the tubular body portion to each of the end plugs in such a fashion that excess load is applied to the end plugs when they are in the open configuration with a force and travel sufficient to close the pivotally secured end plugs, a lever pivot assembly to actuate said power spring, a lanyard to hold the end plugs in an open position, and a lanyard securing means, comprising the steps of:

preloading the sampler end plugs from a travel configuration in which they are closed by means of pivoting the lever and engaging the same to a power drivingly pivot both end plugs, thereafter securing the lanyard to the lanyard securing means, transferring the load to the lanyard to go in tension and hold the end plugs in the open configuration, and releasing the securing means for the lanyard at a desired depth in a fluid to encapsulate a sample of the same.

* * * * *